(12) United States Patent
Yao et al.

(10) Patent No.: US 10,317,556 B2
(45) Date of Patent: Jun. 11, 2019

(54) NON-LINEAR ACOUSTIC FORMATION EVALUATION

(71) Applicant: BAKER HUGHES INCORPORATED, Houston, TX (US)

(72) Inventors: Xiaochu Yao, Houston, TX (US); Wei Han, Sugar Land, TX (US); Quming Zhou, Houston, TX (US); Hao Zhang, The Woodlands, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 79 days.

(21) Appl. No.: 15/010,730

(22) Filed: Jan. 29, 2016

(65) Prior Publication Data
US 2017/0212262 A1    Jul. 27, 2017

Related U.S. Application Data
(60) Provisional application No. 62/286,932, filed on Jan. 25, 2016.

(51) Int. Cl.
*G01V 1/40* (2006.01)
*G01V 1/50* (2006.01)

(52) U.S. Cl.
CPC ............ *G01V 1/50* (2013.01); *G01V 1/40* (2013.01); *G01V 2210/62* (2013.01); *G01V 2210/6244* (2013.01)

(58) Field of Classification Search
CPC ... G01V 1/40; G01V 1/44; G01V 1/50; G01V 2210/62; G01V 2210/624; G01V 2210/6244

(Continued)

(56) References Cited

U.S. PATENT DOCUMENTS

| 5,485,431 A | * | 1/1996 | Johnson | G01V 1/44 367/30 |
| 5,619,475 A | * | 4/1997 | Winkler | G01H 5/00 181/105 |

(Continued)

OTHER PUBLICATIONS
Xiang, Yanxun et al., "Effect of precipitate-dislocation interactions on generation of nonlinear Lamb waves in creep-damaged metallic alloys," Jnl of Applied Physics 111, 104905, 9 pp. (2012).

*Primary Examiner* — Ian J Lobo
(74) *Attorney, Agent, or Firm* — Mossman, Kumar & Tyler P.C.

(57) ABSTRACT

Systems, devices, and methods for evaluating a volume of interest of an earth formation. Methods include estimating a parameter of interest of a volume of the formation using a value of a signal property (frequency amplitude) for a second harmonic mode signal component of a detected acoustic signal from the volume. Methods may include activating a transmitter to propagate an acoustic wave through the volume; producing the detected acoustic signal at a receiver responsive to the acoustic wave; and identifying the fundamental mode signal and the second harmonic mode signal associated with the detected acoustic signal. Methods include estimating an acoustic wave non-linearity parameter ($\beta$) for the volume using a relationship between the value of the signal property of the second harmonic mode signal component and a value of the signal property for a fundamental mode signal component of the detected acoustic signal.

13 Claims, 7 Drawing Sheets

(58) Field of Classification Search
USPC .............................................. 367/25, 31, 32
See application file for complete search history.

(56) References Cited

U.S. PATENT DOCUMENTS

| | | | |
|---|---|---|---|
| 6,614,717 B1 * | 9/2003 | Khan | ..................... G01V 1/005 367/46 |
| 6,789,018 B1 * | 9/2004 | Khan | ....................... G01V 1/28 702/2 |
| 8,767,506 B2 * | 7/2014 | Froelich | .............. E21B 47/0005 367/35 |
| 2008/0019216 A1 | 1/2008 | Leggett, III et al. | |
| 2011/0080803 A1 | 4/2011 | Vu et al. | |
| 2014/0060822 A1 | 3/2014 | Segal | |
| 2015/0103624 A1 | 4/2015 | Thompson et al. | |
| 2015/0268367 A1 | 9/2015 | Khajeh et al. | |

* cited by examiner

NON-LINEAR ACOUSTIC FORMATION EVALUATION

CROSS-REFERENCE TO RELATED APPLICATIONS

This application claims priority from United States Provisional Patent Application Ser. No. 62/286,932 filed on Jan. 25, 2016, the disclosure of which is incorporated herein by reference in its entirety.

FIELD OF THE DISCLOSURE

In one aspect, this disclosure relates generally to downhole acoustic logging in a borehole intersecting a volume of interest of an earth formation. Acoustic signals propagating through the volume are detected and processed to estimate a parameter of interest of the volume.

BACKGROUND OF THE DISCLOSURE

Geologic formations are used for many purposes such as hydrocarbon production, geothermal production and carbon dioxide sequestration. Boreholes are typically drilled into the earth in order to intersect and access the formations.

Acoustic borehole logging instruments are used to estimate parameters of interest of the formation. For example, these downhole tools may measure velocities of earth formations in one or more modes of acoustic energy propagation. Acoustic borehole logging instruments are typically used in liquid-filled boreholes drilled through the earth formations. Velocity is generally determined using these instruments by measuring the time taken by an acoustic energy pulse to traverse a particular distance along the wall of the wellbore. Conventional acoustic logging methods can also measure sound speed and attenuation at a fundamental-mode frequency to estimate parameters of interest (e.g., formation properties).

Hydraulic fracturing and other stimulation techniques may be applied to the formation to facilitate removal of hydrocarbons by fracturing the formation and/or extending existing fractures in the formation. Evaluation of the extent, complexity, and orientation of fractures is relevant to evaluating hydraulic fracturing operations, monitoring the fracture system, and managing operations in the formation.

The estimation of mechanical parameters of an earth formation may also be determined via various downhole operations or by analysis of a sample volume of the formation brought to the surface. These mechanical parameters may be important for many applications such as reservoir stress-state determination, horizontal drilling and hydraulic fracturing design. These parameters include Young's modulus, Poisson's ratio, cohesion, angle of internal friction, Mohr-Coulomb failure envelope, and unconfined compressive strength. Their determination is commonly performed via core sample analysis, including compression tests of core samples at various confining pressures. Characterizing these parameters facilitates optimization of further operations conducted in the formation, such as fracturing operations, drilling, or other exploration or completion operations of a typical oil or gas well.

SUMMARY OF THE DISCLOSURE

In aspects, the present disclosure is related to methods of evaluating an earth formation intersected by a borehole using signals produced in the borehole. In other aspects, the present disclosure is related to evaluating the earth formation by testing materials retrieved from the formation.

Methods of the present disclosure include estimating a parameter of interest of a volume of the formation using a value of a signal property for a second harmonic mode signal component of a detected acoustic signal from the volume. The volume may be a subterranean volume intersected by a borehole or a volume retrieved from the formation. The signal property may comprise at least frequency amplitude. Methods may include activating a transmitter to propagate an acoustic wave through the volume; producing the detected acoustic signal at a receiver responsive to the acoustic wave; and identifying the fundamental mode signal and the second harmonic mode signal associated with the detected acoustic signal.

Estimating the parameter of interest may include estimating an acoustic wave non-linearity parameter ($\beta$) for the volume using a relationship between the value of the signal property of the second harmonic mode signal component and a value of the signal property for a fundamental mode signal component of the detected acoustic signal; and estimating the parameter of interest using a correlation between the acoustic wave non-linearity parameter ($\beta$) and the parameter of interest. The relationship may comprise a ratio of the value of the signal property of the second harmonic mode signal component and the value of the signal property for a fundamental mode signal component. The parameter of interest may be at least one of: i) porosity; ii) tortuosity; iii) water saturation; iv) oil saturation; v) formation stress.

Methods may include positioning at least one of the transmitter proximate to a wall of the borehole for transmission. The volume may be remote from the formation while activating the transmitter and producing the signal. In example, the volume may be a core sample. The detected acoustic signal may be detected during a downhole operation in the formation, the downhole operation comprising at least one of: i) performing a drilling operation, ii) wireline logging, and iii) cement evaluation. Methods may include determining an optimal input voltage for receiver electronics producing the detected acoustic signal at a receiver to optimize non-linear harmonic interference to the second harmonic mode by: estimating initial acoustic wave non-linearity parameters ($\beta_n$) for the volume at each of a plurality input voltages until a stability condition is met for the initial acoustic wave non-linearity parameters ($\beta_n$); and using at least one of the plurality of voltages corresponding to the stability condition being met for producing the detected acoustic signal. The stability condition may include a variation measure between initial acoustic wave non-linearity parameters ($\beta_n$) corresponding to successive voltages is less than a threshold value.

Methods may include activating a transmitter to propagate an acoustic wave through the volume at each of a plurality of frequencies; generating acoustic signals at a receiver responsive to the acoustic wave corresponding to each of the plurality of frequencies; identifying one of the acoustic signals as meeting selection criteria for a detected acoustic signal; and producing the identified one of the acoustic signals as the detected acoustic signal.

Methods may include estimating the parameter of interest of the volume in dependence upon the value of the signal property for the second harmonic mode signal component and a value of at least one of: i) a shear wave slowness for the volume; and ii) a compressional wave slowness for the volume.

Apparatus embodiments may include at least one processor configured to estimate a parameter of interest of the volume using a value of a signal property for a second harmonic mode signal component of a detected acoustic signal from the volume. Apparatus embodiments may include at least one transmitter and at least one receiver associated with a tool body on a carrier. The transmitter and receiver(s) may be implemented as transducers, and may be the same transducer or a different transducer.

The transducer(s) may be on a tool and the at least one processor may be on the tool or communicatively coupled to the tool to receive signal information. The at least one processor may be at least one of: i) downhole, and ii) at the surface. The at least one processor may be configured by providing computer program instructions on a non-transitory computer readable medium accessible to the at least one processor, wherein execution of the computer program instructions by the at least one processor causes methods of the present disclosure to be carried out.

Embodiments according to the present disclosure may include apparatus for evaluating a formation intersected by a borehole, comprising: a processor; a non-transitory computer-readable medium; and a program stored by the non-transitory computer-readable medium comprising instructions that, when executed, cause the processor to perform a method as described herein.

Example features of the disclosure have been summarized rather broadly in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein.

DETAILED DESCRIPTION

Figure 1A:
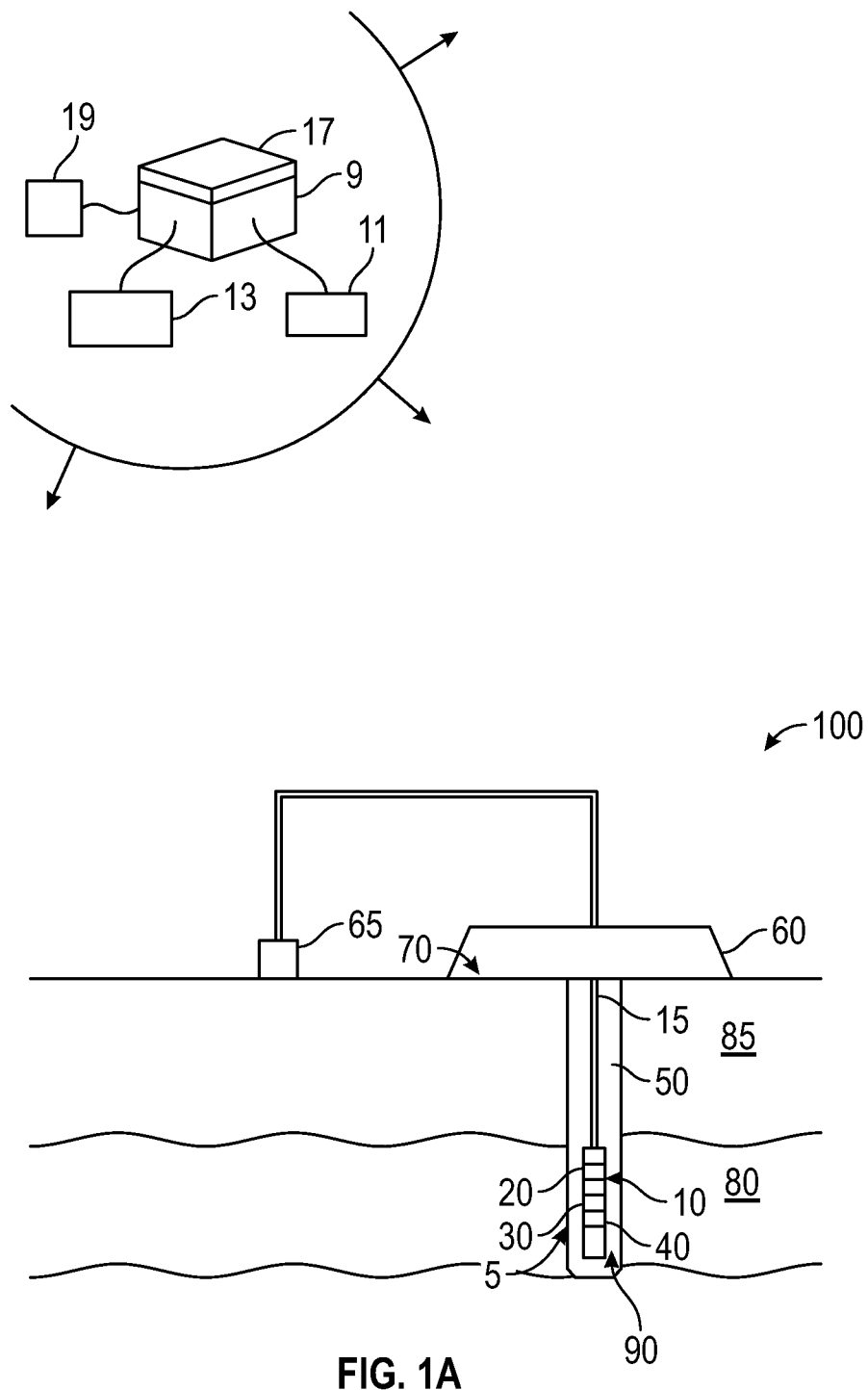
FIG. 1A schematically illustrates an acoustic wellbore logging system in accordance with embodiments of the present disclosure.

Aspects of the present disclosure include acoustic evaluation of a volume of interest of an earth formation. Methods use higher-order harmonics to evaluate formation properties from the frequency domain responses of received signals by measuring the harmonic-mode frequency amplitudes and the fundamental-mode central frequency amplitudes.

Aspects of the present disclosure include estimating an acoustic wave non-linearity parameter ($\beta$) for the volume and using the acoustic wave non-linearity parameter ($\beta$) to evaluate a volume of interest of an earth formation. Evaluation may include estimating one or more parameters of interest of the volume or the formation (e.g., formation properties).

When acoustic waves with a center frequency propagate through a formation, they generate higher-order harmonics due to the wave distortion associated with the inherent non-linearity of the formation. This non-linearity is caused by formation properties such as porosity, tortuosity, saturation, fluid properties, and stress. The present disclosure estimates a parameter of interest characterizing this non-linearity and uses this measure to estimate the parameter of interest.

Techniques of the present disclosure employ higher-order harmonics to evaluate formation properties from the frequency domain responses of received signals by measuring the harmonic-mode frequency amplitudes and the fundamental-mode central frequency amplitudes.

Although conventional methods are available to measure at least some of the formation parameters, aspects disclosed herein display several advantages over the prior art. For example, conventional acoustic formation evaluation relies on sound speed and attenuation measurements. The sound wave from a transmitter creates compressional and shear waves within the formation. Compressional waves arrive at a receiver before the shear waves. The travel time of the compressional waves may be used to calculate porosity. However, the formation matrix, fluid, and porosity affect the acoustic tool response. In formations with complex lithology and pore structures, such as shale reservoirs, porosity estimation based on travel time of the compressional wave can introduce significant uncertainties, which may escalate the complexity of the operation and increase the likelihood of error.

As shown herein below, non-linear acoustic measurements, which present greater sensitivity and better resolution, can enable detection of small porosity changes in an earth formation, different fluid saturation status, and local formation heterogeneity, and also facilitate the use of conventional acoustic logs. The non-linearity phenomena of the formation induced by acoustic wave propagation are highly correlated with porosity, as demonstrated by preliminary laboratory results obtained from rock samples with different types of lithology and a wide porosity range (e.g., 12 to 27 percent). The acoustic wave non-linearity parameter ($\beta$) has also been proven to be very sensitive to material microstructure imperfections such as dislocations, microvoids, and precipitates when characterizing microstructure degradation, which cannot be detected by conventional linear acoustic measurements.

For acoustic wave propagation in an unbounded medium without body force, the one dimensional ('1-D') non-linear wave equation is given by $$\frac{\partial^2 u}{\partial t^2} = c_L^2 \left\{ 1 - \beta \left( \frac{\partial^2 u}{\partial x^2} \right) \right\} \frac{\partial^2 u}{\partial x^2}, \quad (1)$$

where $c_L$ is longitudinal wave velocity, and u, x, and t are displacement, position, and time, respectively. $\beta$ is the acoustic wave non-linearity parameter, the material non-linear parameter that is an important indicator of the rock formation porosity and other formation properties. The non-linear parameter $\beta$ is given by a combination of linear and non-linear material properties $$\beta = -\left(\frac{3C_{11} + C_{111}}{\sigma_1 + C_{11}}\right), \quad (2)$$

where $C_{11}$ and $C_{111}$ are second- and third-order Brugger elastic constants. $\sigma_1$ is the initial stress in the solid. Eq. (2) indicates that the non-linear parameter $\beta$ is dependent on the higher-order elastic constants and initial stress of the solid.

Consider the solution of Eq. (1), subject to the initial condition that a sinusoidal wave given by $u=A_1 \cos(wt)$ is launched at $x=0$. Using perturbation techniques, it can be shown that, up to the third order, the solution is of the form:

$$u(x, t) = A_1\cos(kx - wt) + A_2\cos^2(kx - wt + \varphi_1) + \ldots \quad (3)$$

where $$A_2 = -\frac{\beta A_1^2 k^2 x}{8}. \quad (4)$$

The second term, $A_2$, in Eq. (3) represents the second harmonic component, and its magnitude depends on $\beta$, the non-linear parameter. $\beta$ can be calculated from the magnitudes of the base mode and the second harmonic generation, as shown in Eq. (4). In alignment with the cumulative nature of second harmonic generation, the magnitude of harmonic waves depends on the medium's material properties, represented by $\beta$, and grows linearly with propagation distance x. In signal measurement, the cumulative properties of non-linear harmonics may be useful in practical application, because these properties facilitate separation of the signal from background noise.

It is noted that $A_2$ is also proportional to the amplitude of the base- or sub-harmonic mode signal $A_1$ and the acoustic wave-number k, where in complex form, $$k=2\pi f/c-j\alpha,$$

where f is frequency, c and a are the p-wave velocity and attenuation coefficient in the formation. This proportional relationship suggests that the non-linear parameter is also affected by frequency and formation acoustic properties, in addition to the static displacement $A_1$ that is induced by the material non-linearity. In many formations, especially acoustically slow and soft formations, acoustic waves may be severely attenuated, resulting in a frequency downshift in the received signals compared to the excitation frequency. The acoustic wave non-linearity parameter ($\beta$) may be determined by measuring the absolute amplitudes of the fundamental mode signal $A_1$ and the second harmonic mode signal $A_2$, or $$\beta = \frac{8A_2}{A_1^2 k^2 x}. \quad (5)$$

Because the wavenumber k and the propagation distance x are constants for a given frequency and formation sample, the modal amplitude $A_2/A_1^2$ is representative of the relative non-linearity of a sample, $$\beta \propto \frac{A_2}{A_1^2}. \quad (6)$$

In practice, a narrow-band bulk longitudinal acoustic wave may be excited by a transmitter and propagated through a rock sample. Signals are received by a broad-band receiver. Signal processing of the received signal may be conducted to gate the first arrival pulse and determine the frequency contents of the fundamental mode and the second harmonic generation in rocks. The acoustic wave non-linearity parameter ($\beta$) may be calculated from the amplitudes of the fundamental frequency and the second harmonic frequency to indicate material non-linearity.

The electronic driver and receiver system may be calibrated to minimize the instrument non-linear harmonic interference to the harmonic mode generated in the formation. One method may use electronically matching circuits to the transmitter and receiver. System non-linearity may be checked and a minimum drive voltage input selected by increasing the drive voltage until determining that the acoustic wave non-linearity parameter ($\beta$) has become sufficiently stable (see Appendix).

The acoustic wave non-linearity parameter ($\beta$) may be measured at multiple frequencies. That is, measurements may be conducted with acoustic waves at several narrow-band base frequencies and their high-order frequencies by activating the transmitter to propagate an acoustic wave through the volume at each of a plurality of frequencies and generating signals at a receiver responsive to the acoustic wave corresponding to each of the plurality of frequencies. An optimal operating frequency may be selected from the multiple frequencies to avoid instrument high-harmonic response, account for formation attenuation, and enable good signal sensitivity by identifying one of the acoustic signals as meeting selection criteria for a detected acoustic signal; and producing the identified one of the acoustic signals as the detected acoustic signal.

The acoustic wave non-linearity parameter ($\beta$) may further be used to determine rock porosity and monitor the quality of a core sample. Lab results have shown good correlations to a wide porosity range (12 to 27%) for different rock core samples (see discussion with respect to FIG. 8, below). Recent lab data have also shown that the acoustic wave non-linearity parameter ($\beta$) is sensitive to small changes in porosity and appears to correlate well with compressional velocities. It is projected that the acoustic wave non-linearity parameter ($\beta$) is similarly affected by other formation properties (fluid type, saturation, tortuosity, etc.). Characterization of the behavior of parameter ($\beta$) with respect to these effects should be straightforward. The acoustic wave non-linearity parameter ($\beta$) may be further correlated or combined with linear acoustic compressional and shear velocity measurements. This effort would help expand downhole acoustic tool capability and enhance the reliability of formation property measurement and evaluation. Estimating the parameter of interest of the volume may be carried out in dependence upon the value of the signal property for the second harmonic mode signal component and a value of at least one of: i) a shear wave slowness for the volume; and ii) a compressional wave slowness for the volume. For example, if the results of models using the respective measurements deviate, a flag may result, prompting further measurements or processing. Additionally, missing or unreliable data in estimates from measurements of one type may be filled with those of another. In further implementations, the information from each measurement type may be combined as a weighted function to arrive at the estimated parameter of interest.

Aspects of the present disclosure relate to exciting, calibrating, and measuring non-linearity parameters, which may then be used to evaluate formation properties. The present disclosure sets forth novel techniques to estimate important petrophysical properties, such as, for example, porosity, fluids saturation, and rock mechanical properties based on non-linear acoustic phenomena for logging and formation evaluation applications, the non-linear parameter ($\beta$) and/or its variation over time or frequency can be used to monitor the quality of a core sample in a downhole coring device, or to evaluate core samples at the surface.

Embodiments may include using at least one acoustic sensor to produce acoustic information responsive to an acoustic wave from the earth formation. The sensor may include at least one acoustic transmitter and at least one acoustic receiver, which may be implemented as transducers. The acoustic transmitter may be a monopole or directional transmitter. In some implementations, the same transducer may serve as both transmitter and receiver. The information is indicative of a parameter of interest. The term "information" as used herein includes any form of information (analog, digital, EM, printed, etc.), and may include one or more of: raw data, processed data, and signals.

Methods may include estimating a parameter of interest from the information, evaluating the formation using the parameter of interest, and performing further borehole operations in dependence upon the evaluation or the parameter of interest. In particular embodiments, a state of drilling operations, characteristics of the borehole or formation, or orientation of components of the downhole tool may be estimated using the parameter of interest, and then used in performing an operation as described above.

FIG. 1A schematically illustrates a downhole acoustic logging system 100 having a downhole tool 10 configured to acquire information using a sensor 5, comprising at least one acoustic transmitter 40 and at least one acoustic receiver 20, while in a borehole 50 in an earth formation 80 and estimate a parameter of interest of a volume of interest of the formation 80. The at least one acoustic transmitter 40 and at least one acoustic receiver 20 may include one or more transducers. An acoustic transducer array can be used with one or more transmitters paired with multiple receivers to obtain parameter mapping for the interested formation. The sensor 5 may include a plurality of transducers in an azimuthal array about the circumference of the tool or a transducer capable of sending acoustic pulses to and receiving signals from a plurality of azimuthal orientations via the use of beam-forming.

The system 100 may include a conventional derrick 60 erected on a derrick floor 70. A conveyance device (carrier 15) which may be rigid or non-rigid, may be configured to convey the downhole tool 10 in the wellbore 50 intersecting the earth formation 80. Drilling fluid ('mud') 90 may be present in the borehole 50. The carrier 15 may be a drill string, coiled tubing, a slickline, an e-line, a wireline, etc. Downhole tool 10 may be coupled or combined with additional tools, including, e.g., some or all the information processing system (inset). Thus, depending on the configuration, the tool 10 may be used during drilling and/or after the wellbore 50 has been formed. While a land system is shown, the teachings of the present disclosure may also be utilized in offshore or subsea applications. The carrier 15 may include embedded conductors for power and/or data for providing signal and/or power communication between the surface and downhole equipment (e.g., a seven conductor cable). The carrier 15 may include a bottom hole assembly, which may include a drilling motor for rotating a drill bit.

A surface control system 65 receives signals from downhole sensor 40 and other sensors used in the system 100 and processes such signals according to programmed instructions provided to the surface control system 65. The surface control system 65 may display desired parameters and other information on a display/monitor that is utilized by an operator. The surface control system 65 may further communicate with a downhole control system 30 at a suitable location on downhole tool 10. The surface control system 65 may process data relating to the operations and data from the sensor 40, and may control one or more downhole operations performed by system 100.

In one embodiment, electronics associated with sensors 40 may be configured to record and/or process the information obtained. Certain embodiments of the present disclosure may be implemented with a hardware environment 21 that includes an information processor 17, an information storage medium 13, an input device 11, processor memory 9, and may include peripheral information storage medium 19. The hardware environment may be in the well, at the rig, or at a remote location. Moreover, the several components of the hardware environment may be distributed among those locations. The input device 11 may be any data reader or user input device, such as data card reader, keyboard, USB port, etc. The information storage medium 13 stores information provided by the detectors. Information storage medium 13 may include any non-transitory computer-readable medium for standard computer information storage, such as a USB drive, memory stick, hard disk, removable RAM, EPROMs, EAROMs, flash memories and optical disks or other commonly used memory storage system known to one of ordinary skill in the art including Internet based storage. Information storage medium 13 stores a program that when executed causes information processor 17 to execute the disclosed method. Information storage medium 13 may also store the formation information provided by the user, or the formation information may be stored in a peripheral information storage medium 19, which may be any standard computer information storage device, such as a USB drive, memory stick, hard disk, removable RAM, or other commonly used memory storage system known to one of ordinary skill in the art including Internet based storage. Information processor 17 may be any form of computer or mathematical processing hardware, including Internet based hardware. When the program is loaded from information storage medium 13 into processor memory 9 (e.g. computer RAM), the program, when executed, causes information processor 17 to retrieve detector information from either information storage medium 13 or peripheral information storage medium 19 and process the information to estimate a parameter of interest. Information processor 17 may be located on the surface or downhole.

The term "information" as used herein includes any form of information (analog, digital, EM, printed, etc.). As used herein, a processor is any information processing device that transmits, receives, manipulates, converts, calculates, modulates, transposes, carries, stores, or otherwise utilizes information. In several non-limiting aspects of the disclosure, an information processing device includes a computer that executes programmed instructions for performing various methods. These instructions may provide for equipment operation, control, data collection and analysis and other functions in addition to the functions described in this disclosure. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on.

In one embodiment, electronics associated with the transducers (described in further detail below with respect to FIG. 2) may be configured to take measurements at a plurality of azimuthal orientations as the tool moves along the longitudinal axis of the borehole ('axially') using sensor 40. These measurements may be substantially continuous, which may be defined as being repeated at very small increments of depth and azimuth, such that the resulting information has sufficient scope and resolution to provide an image of borehole parameters (e.g., electrical properties of the formation at the borehole.

In other embodiments, electronics may be located elsewhere (e.g., at the surface, or remotely). To perform the treatments during a single trip, the tool may use a high bandwidth transmission to transmit the information acquired by sensor 40 to the surface for analysis. For instance, a communication line for transmitting the acquired information may be an optical fiber, a metal conductor, or any other suitable signal conducting medium. It should be appreciated that the use of a "high bandwidth" communication line may allow surface personnel to monitor and control operations in "near real-time."

One point of novelty of the system illustrated in FIG. 1A is that the at least one processor may be configured to perform certain methods (discussed below) that are not in the prior art. A surface control system or downhole control system may be configured to control the tool described above and any incorporated sensors and to estimate a parameter of interest according to methods described herein.

Figure 1B:
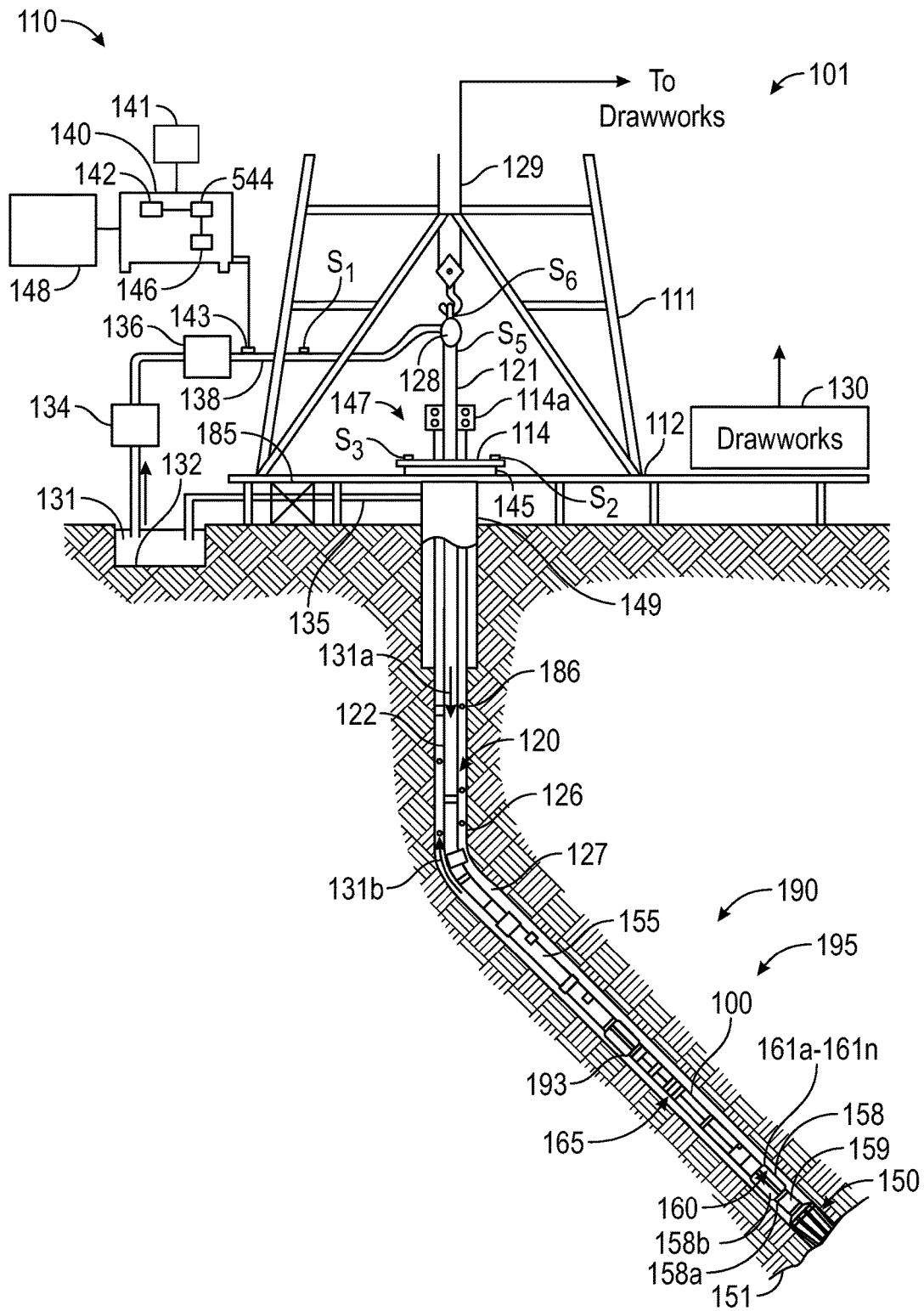
FIG. 1B is a schematic diagram of an example drilling system in accordance with embodiments of the present disclosure.

Aspects of the present disclosure are subject to application in various different embodiments. In some general embodiments, carrier 15 is implemented as a tool string of a drilling system, and the acoustic wellbore logging may be characterized as "logging-while-drilling" (LWD) or "measurement-while-drilling" (MWD) operations. FIG. 1B shows an exemplary embodiment of a system for evaluation of an earth formation using measurements from an acoustic logging system. The system 101 includes a carrier 111 that is shown disposed in a wellbore or borehole 126 that penetrates at least one earth formation 195. The system 101 also includes a tool 110 configured for taking acoustic measurements in the borehole.

As described herein, "borehole" or "wellbore" refers to a single hole that makes up all or part of a drilled well. Depending on the configuration, the system 101 may be used during drilling and/or after the wellbore 112 has been formed, including, in some instances after the installation of casing or production infrastructure. While a land system is shown, the teachings of the present disclosure may also be utilized in offshore or subsea applications. As described herein, "formations" refer to the various features and materials that may be encountered in a subsurface environment and surround the borehole. The term "information" includes, but is not limited to, raw data, processed data, and signals.

FIG. 1B is a schematic diagram of an exemplary drilling system 100 according to one embodiment of the disclosure. FIG. 1 shows a drill string 120 that includes a bottomhole assembly (BHA) 190 conveyed in a borehole 126. The drilling system 100 includes a conventional derrick 111 erected on a platform or floor 112 which supports a rotary table 114 that is rotated by a prime mover, such as an electric motor (not shown), at a desired rotational speed. A tubing (such as jointed drill pipe 122), having the drilling assembly 190, attached at its bottom end extends from the surface to the bottom 151 of the borehole 126. A drill bit 150, attached to drilling assembly 190, disintegrates the geological formations when it is rotated to drill the borehole 126. The drill string 120 is coupled to a drawworks 130 via a Kelly joint 121, swivel 128 and line 129 through a pulley. Drawworks 130 is operated to control the weight on bit ("WOB"). The drill string 120 may be rotated by a top drive (not shown) instead of by the prime mover and the rotary table 114. Alternatively, a coiled-tubing may be used as the tubing 122. A tubing injector 114a may be used to convey the coiled-tubing having the drilling assembly attached to its bottom end. The operations of the drawworks 130 and the tubing injector 114a are known in the art and are thus not described in detail herein.

A suitable drilling fluid 131 (also referred to as the "mud") from a source 132 thereof, such as a mud pit, is circulated under pressure through the drill string 120 by a mud pump 134. The drilling fluid 131 passes from the mud pump 134 into the drill string 120 via a desurger 136 and the fluid line 138. The drilling fluid 131a from the drilling tubular discharges at the borehole bottom 151 through openings in the drill bit 150. The returning drilling fluid 131b circulates uphole through the annular space 127 between the drill string 120 and the borehole 126 and returns to the mud pit 132 via a return line 135 and drill cutting screen 185 that removes the drill cuttings 186 from the returning drilling fluid 131b. A sensor S1 in line 138 provides information about the fluid flow rate. A surface torque sensor S2 and a sensor S3 associated with the drill string 120 respectively provide information about the torque and the rotational speed of the drill string 120. Tubing injection speed is determined from the sensor S5, while the sensor S6 provides the hook load of the drill string 120.

Well control system 147 is placed at the top end of the borehole 126. The well control system 147 includes a surface blow-out-preventer (BOP) stack 115 and a surface choke 149 in communication with a wellbore annulus 127. The surface choke 149 can control the flow of fluid out of the borehole 126 to provide a back pressure as needed to control the well.

In some applications, the drill bit 150 is rotated by only rotating the drill pipe 122. However, in many other applications, a downhole motor 155 (mud motor) disposed in the BHA 190 also rotates the drill bit 150. The rate of penetration (ROP) for a given BHA largely depends on the WOB or the thrust force on the drill bit 150 and its rotational speed.

A surface control unit or controller 140 receives signals from the downhole sensors and devices via a sensor 143 placed in the fluid line 138 and signals from sensors S1-S6 and other sensors used in the system 100 and processes such signals according to programmed instructions provided to the surface control unit 140. The surface control unit 140 displays desired drilling parameters and other information on a display/monitor 141 that is utilized by an operator to control the drilling operations. The surface control unit 140 may be a computer-based unit that may include a processor 142 (such as a microprocessor), a storage device 144, such as a solid-state memory, tape or hard disc, and one or more computer programs 146 in the storage device 144 that are accessible to the processor 142 for executing instructions contained in such programs. The surface control unit 140 may further communicate with a remote control unit 148. The surface control unit 140 may process data relating to the drilling operations, data from the sensors and devices on the surface, data received from downhole, and may control one or more operations of the downhole and surface devices. The data may be transmitted in analog or digital form.

The BHA 190 may also contain formation evaluation sensors or devices (also referred to as measurement-while-drilling ("MWD") or logging-while-drilling ("LWD") sensors) determining resistivity, density, porosity, permeability, acoustic properties, nuclear-magnetic resonance properties, formation pressures, properties or characteristics of the fluids downhole and other desired properties of the formation 195 surrounding the BHA 190. Such sensors are generally known in the art and for convenience are generally denoted herein by numeral 165, and include counterparts to the sensor(s) 40 described above with respect to FIG. 1A. The BHA 190 may further include a variety of other sensors and devices 159 for determining one or more properties of the BHA 190 (such as vibration, bending moment, acceleration, oscillations, whirl, stick-slip, etc.), drilling operating parameters (such as weight-on-bit, fluid flow rate, pressure, temperature, rate of penetration, azimuth, tool face, drill bit rotation, etc.). For convenience, all such sensors are denoted by numeral 159.

The BHA 190 may include a steering apparatus or tool 158 for steering the drill bit 150 along a desired drilling path. In one aspect, the steering apparatus may include a steering unit 160, having a number of force application members 161*a*-161*n*. The force application members may be mounted directly on the drill string, or they may be at least partially integrated into the drilling motor. In another aspect, the force application members may be mounted on a sleeve, which is rotatable about the center axis of the drill string. The force application members may be activated using electro-mechanical, electro-hydraulic or mud-hydraulic actuators. In yet another embodiment the steering apparatus may include a steering unit 158 having a bent sub and a first steering device 158*a* to orient the bent sub in the wellbore and the second steering device 158*b* to maintain the bent sub along a selected drilling direction. The steering unit 158, 160 may include near-bit inclinometers and magnetometers.

The drilling system 100 may include sensors, circuitry and processing software and algorithms for providing information about desired drilling parameters relating to the BHA, drill string, the drill bit and downhole equipment such as a drilling motor, steering unit, thrusters, etc. Many current drilling systems, especially for drilling highly deviated and horizontal wellbores, utilize coiled-tubing for conveying the drilling assembly downhole. In such applications a thruster may be deployed in the drill string 190 to provide the required force on the drill bit.

Exemplary sensors for determining drilling parameters include, but are not limited to drill bit sensors, an RPM sensor, a weight on bit sensor, sensors for measuring mud motor parameters (e.g., mud motor stator temperature, differential pressure across a mud motor, and fluid flow rate through a mud motor), and sensors for measuring acceleration, vibration, whirl, radial displacement, stick-slip, torque, shock, vibration, strain, stress, bending moment, bit bounce, axial thrust, friction, backward rotation, BHA buckling, and radial thrust. Sensors distributed along the drill string can measure physical quantities such as drill string acceleration and strain, internal pressures in the drill string bore, external pressure in the annulus, vibration, temperature, electrical and magnetic field intensities inside the drill string, bore of the drill string, etc. Suitable systems for making dynamic downhole measurements include COPILOT, a downhole measurement system, manufactured by BAKER HUGHES INCORPORATED.

The drilling system 100 can include one or more downhole processors at a suitable location such as 193 on the BHA 190. The processor(s) can be a microprocessor that uses a computer program implemented on a suitable non-transitory computer-readable medium that enables the processor to perform the control and processing. The non-transitory computer-readable medium may include one or more ROMs, EPROMs, EAROMs, EEPROMs, Flash Memories, RAMs, Hard Drives and/or Optical disks. Other equipment such as power and data buses, power supplies, and the like will be apparent to one skilled in the art. In one embodiment, the MWD system utilizes mud pulse telemetry to communicate data from a downhole location to the surface while drilling operations take place. While a drill string 120 is shown as a conveyance device for sensors 165, it should be understood that embodiments of the present disclosure may be used in connection with tools conveyed via rigid (e.g. jointed tubular or coiled tubing) as well as non-rigid (e. g. wireline, slickline, e-line, etc.) conveyance systems. The drilling system 100 may include a bottomhole assembly and/or sensors and equipment for implementation of embodiments of the present disclosure on either a drill string or a wireline.

A point of novelty of the system illustrated in FIG. 1 is that the surface processor 142 and/or the downhole processor 193 are configured to perform certain methods (discussed below) that are not in the prior art. Surface processor 142 or downhole processor 193 may be configured to control mud pump 134, drawworks 130, rotary table 114, downhole motor 155, other components of the BHA 190, or other components of the drilling system 100. Surface processor 142 or downhole processor 193 may be configured to control sensors described above and to estimate a parameter of interest according to methods described herein.

Control of these components may be carried out using one or more models using methods described below. For example, surface processor 142 or downhole processor 193 may be configured to modify drilling operations i) autonomously upon triggering conditions, ii) in response to operator commands, or iii) combinations of these. Such modifications may include changing drilling parameters, mud parameters, and so on. Control of these devices, and of the various processes of the drilling system generally, may be carried out in a completely automated fashion or through interaction with personnel via notifications, graphical representations, user interfaces and the like. Additionally or alternatively, surface processor or downhole processor may be configured for the creation of the model. Reference information accessible to the processor may also be used.

In some general embodiments, surface processor 142, downhole processor 193, or other processors (e.g. remote processors) may be configured to use at least one sensor to produce a corresponding signal, responsive in part to a reflection of an emitted wave, from each of a plurality of azimuthally distributed orientations about a BHA. In some general embodiments, surface processor 142, downhole processor 193, or other processors (e.g. remote processors) may be configured to operate the tool 101 to excite and measure acoustic signals.

Mathematical models, look-up tables, or other models representing relationships between the signals and the values of the formation properties may be used to characterize operations in the formation or the formation itself, optimize one or more operational parameters of a production or development, and so on. The system may carry out these actions through notifications, advice, and/or intelligent control.

Figure 2:
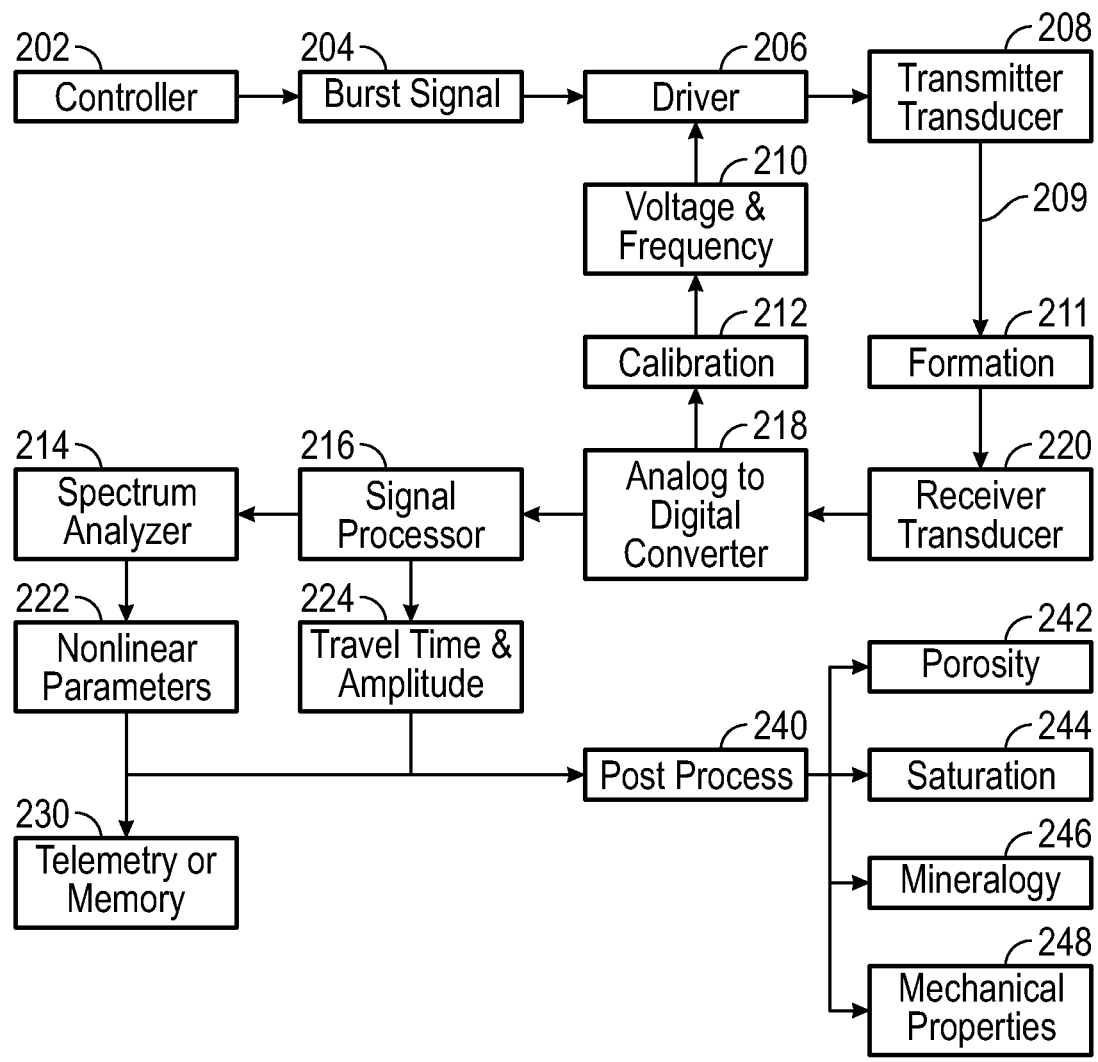
FIG. 2 is a data flow diagram illustrating an example system architecture in accordance with embodiments of the present disclosure.

FIG. 2 is a data flow diagram illustrating an example system architecture in accordance with embodiments of the present disclosure. The system includes a controller 202, a driver 206, a transmitter transducer 208, and a receiver transducer 220. The transmitter transducer 208 and the receiver transducer 220 are each acoustically coupled with a formation 212 (or the retrieved volume, such as a core sample). The transmitter and the receiver may be wet-coupled to the formation via a soft pad or have a fluid (e.g., downhole fluid) between them. The acoustic waves travel in the volume at a known distance.

In operation, the transmitter transducer 208 transmits burst acoustic waves 209 with central frequency $f_0$ to the volume of interest (or target volume of the formation 212). The tone-burst drive may be generated by a function generator and a power amplifier driver. For example, this may be accomplished by using the controller 202 to generate a burst signal 204 which is supplied to the transmitter transducer 208 by the driver 206, which may provide amplification and control (including closed-loop feedback, as described below). The center frequency of the transducer may be from 500 kHz to approximately 2.0 MHz. A narrow-band multiple-cycle tone-burst driver may be set at approximately 300 V peak-to-peak, at a center frequency in the range of 500 kHz to about 1.0 MHz. To minimize reflection interference, the cycle number may be increased to a point where the total burst train wavelength is close to but less than the sample length.

A wide-band receiver (e.g., having −6 dB bandwidth from the fundamental mode center frequency of the transmitted signal) may be preferable for the receiver transducer 220 in some applications. The receiver transducer 220 may have a center frequency approximately twice that of the transmitting center frequency, for instance. In one example, a transducer with an 80 percent bandwidth at 2.25-MHz center frequency may be used to receive the second-order non-linear mode originated from 1.0-MHz excitation.

The signal produced by the receiver transducer 220 is acquired by an analog-to-digital converter ('ADC') 208. The signal emerging from the ADC 208 is a digital signal, which may be operated on, in turn, by various logic modules in signal processor 216. The signals may be amplified using a low-noise preamplifier and filtered (i.e., anti-aliasing or band-pass filter) to remove low-frequency and high-frequency noise outside of the operating band. Travel time and amplitude logic modules may be used to further process the signals. The first arrival signals in the digitized waveform may be gated using a windowing method. The compressional acoustic velocity in the formation may be determined from the first-arrival travel time (less the internal travel time in the transducer and electronics) and the known sample length. The received signal is processed using a window method to extract the first arriving wave.

The signal processor may also send information to the spectrum analyzer 214. The frequency spectrum of the received signal may be built at the central frequency of the fundamental mode $f_0$ and the second harmonic frequency $2f_0$. The amplitude ($A_1$) of the frequency spectrum $f_0$ and the amplitude ($A_2$) at frequency $2f_0$ are recorded (222). The frequency analysis can be run by fast Fourier transform (FFT) with windowing. To reduce transient effects, a first arriving wave is gated using a Tukey window for the frequency analysis—a uniform Tukey window of a constant length may be utilized.

For optimal operation of the system, system calibration must be performed by varying the system input voltage to find the stable optimal zones of $A_2/A_1^2$, by verifying that non-linear parameters do not change with system inputs. Instrument non-linear response can be calibrated and corrected by 1) increasing drive power input to the transducer, 2) estimating parameter β values and estimating their variation (e.g., standard deviation, variance, and so on), and 3) selecting the drive power or voltage that results in a small variation (e.g., less than 10 percent) in value of parameter β for use in formation measurement. The optimal voltage zones may be used in the measurement to obtain more measurement points for averaging. Transducer electronics may include matching driver and receiver circuits to suppress and minimize instrument non-linear responses.

The acoustic wave non-linearity parameter (β) may be estimated by performing the calculation $A_2/A_1^2$, and then used to characterize local formation non-linearity. Formation properties such as porosity and saturation may then be determined from the estimated acoustic wave non-linearity parameter (β) using an inversion model, a template, or a look-up table in a processor. The processor may also calculate porosity from the compressional velocity using an appropriate estimate model. To improve data quality and reliability the processor may correlate and compare the porosities estimated from non-linear parameter and the compressional velocity.

Figure 3:
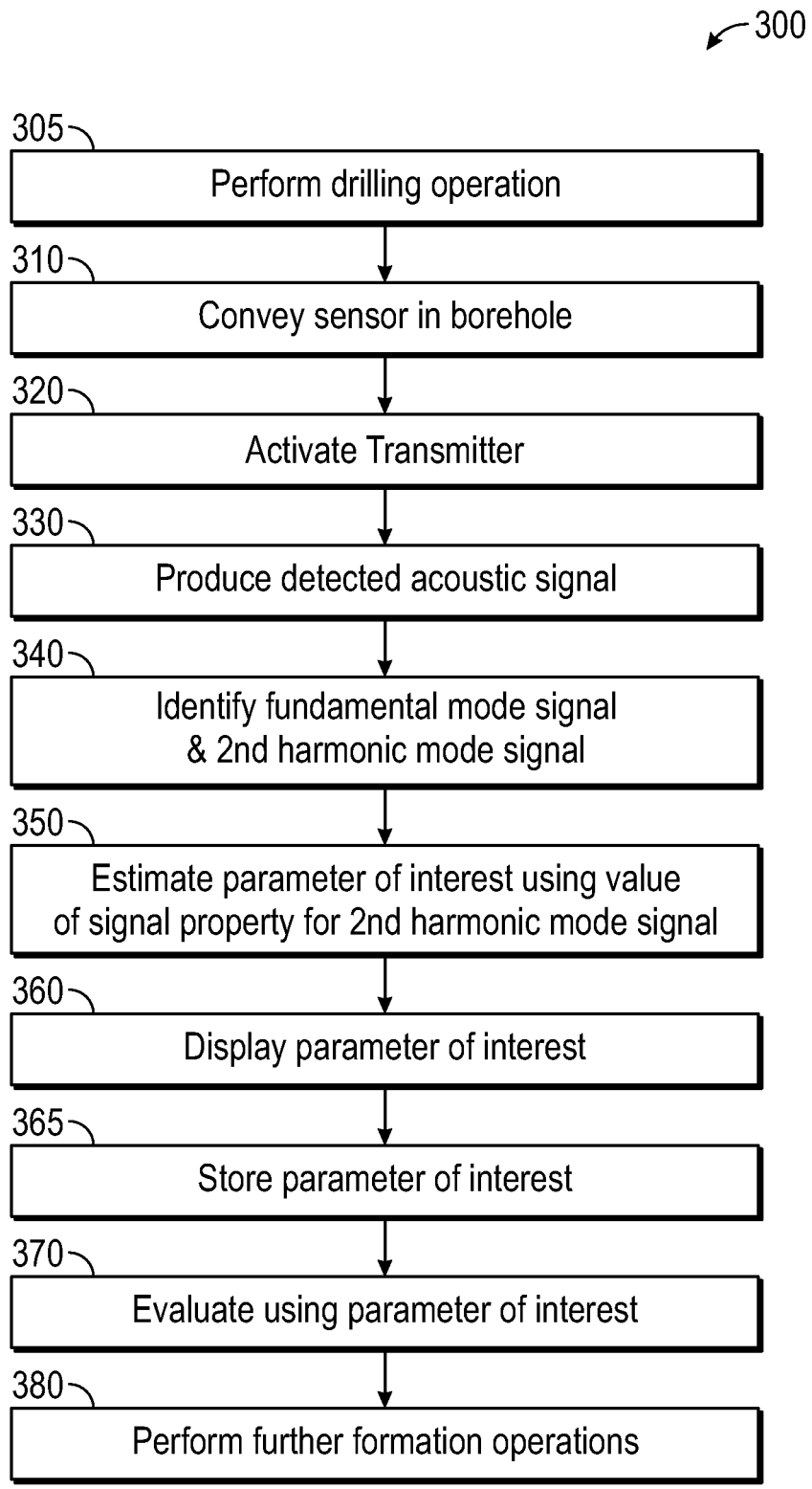
FIG. 3 illustrates a method for evaluating an earth formation intersected by a borehole using signals produced at a plurality of borehole depths by an acoustic sensor in the borehole.

FIG. 3 illustrates a method for evaluating an earth formation intersected by a borehole using signals produced at a plurality of borehole depths by an acoustic sensor in the borehole. Optional step 305 of the method 300 may include performing a drilling operation in a borehole. For example, a drill string may be used to form (e.g., drill) the borehole. Optional step 310 may include conveying at least one acoustic sensor in the borehole proximate a volume of interest of the formation on a conveyance device. The sensor may comprise part of an acoustic logging tool carried on a tool string (e.g., a drill string, wireline, etc).

Optional step 320 of the method 300 may include activating a transmitter of the sensor to propagate an acoustic wave through the volume. The transmitter may send a tone burst of narrow-band waves to the target volume. This may be a long burst pulse with multiple cycles (e.g., approximately 30 cycles and higher) to approximately the length of the formation spacing between the transmitter and the receiver. In some implementations, the wave may be generated at multiple frequencies. In some embodiments, a transducer array consisting of multiple elements is operated with programmable phase delay.

Optional step 330 may include using the at least one sensor to produce a detected acoustic signal at a receiver responsive to the acoustic wave. The acoustic wave may be indicative of a parameter of interest relating to the formation, the borehole, or fluids or equipment therein. The sensor may include a receiving transducer, which may be the same transducer as the transmitting transducer, or a different transducer. The receiver produces an information signal (e.g., an analog or digital electrical signal referred to as a produced detected acoustic signal) which is indicative of the received acoustic wave, such as, for example, by using a transducer and related circuitry (including in some cases one or more processors, e.g., digital signal processors). The produced detected acoustic signal includes any modifications to the transducer signal such as amplification, filtering or other pre-processing by receiver circuitry, including, for example, one or more analog-to-digital converters, digital signal processors, and so on. Optionally, at step 340, the method may be carried out by identifying the fundamental mode signal and the second harmonic mode signal associated with the detected acoustic signal.

Step 350 comprises estimating a parameter of interest of the volume using a value of a signal property for a second harmonic mode signal component of a detected acoustic signal from the volume. Step 350 may be carried out by estimating an acoustic wave non-linearity parameter ($\beta$) for the volume using a relationship between the value of the signal property of the second harmonic mode signal component and a value of the signal property for a fundamental mode signal component of the detected acoustic signal; and estimating the parameter of interest using a correlation between the acoustic wave non-linearity parameter ($\beta$) and the parameter of interest. The signal property may be frequency amplitude, phase, and so on. The relationship may comprise a ratio using the value of the signal property of the second harmonic mode signal component and the value of the signal property for a fundamental mode signal component. The parameter of interest may be determined from the estimated acoustic wave non-linearity parameter ($\beta$) using an inversion model, a template, or a look-up table in a processor. If measurements are repeated at multiple frequencies, the frequency dependence of the non-linear parameter may be used to estimate parameters of interest. In optional step 355, the previous steps may be repeated for a different depth and/or azimuth in the formation.

Optional step 360 comprises displaying the parameter of interest. Optional step 365 comprises storing the parameter of interest. Optional step 370 comprises using the parameter of interest to evaluate the formation, the borehole, or fluids or equipment therein. This may include using the parameter of interest to create a model of the formation. Optional step 380 may include using the parameter of interest, the evaluation, or the model to perform further formation operations in dependence upon the estimated parameter, evaluation, model, or combinations of these.

Further operations may include at least one of: i) extending the borehole; ii) drilling additional boreholes in the formation; iii) performing additional measurements on the formation; iv) estimating additional parameters of the formation; v) installing equipment in the borehole; vi) evaluating the formation; vii) optimizing present or future development in the formation or in a similar formation; viii) optimizing present or future exploration in the formation or in a similar formation; ix) evaluating the formation; and x) producing one or more hydrocarbons from the formation. For example, the method may include commencing, modifying, continuing, or halting one or more drilling or production operations in dependence upon a model of the formation characterizing particular volumes of interest as having particular properties (e.g., values of one or more parameters of interest).

APPENDIX

Tests of the efficacy of non-linear acoustic measurements were conducted on core samples by measuring relative non-linear parameters, and the relative non-linear parameters were correlated with porosity results from nuclear magnetic resonance ('NMR') analysis. These experimental results demonstrate the feasibility of using non-linear acoustic methods for formation porosity characterization.

Figure 4:
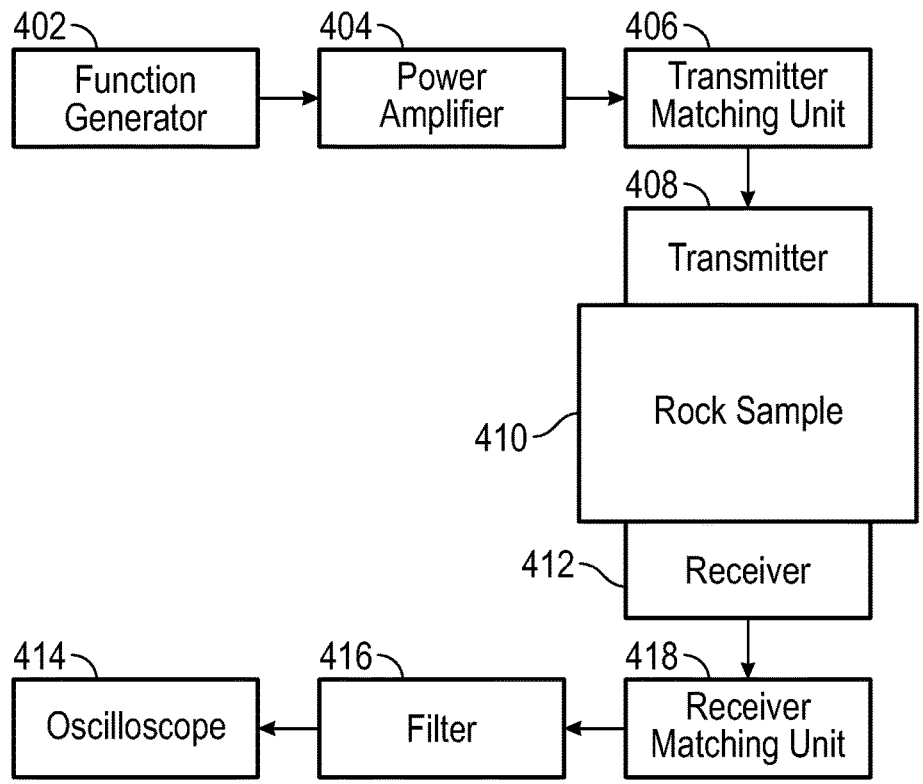
FIG. 4 is a data flow diagram illustrating an example system architecture in accordance with embodiments of the present disclosure.

FIG. 4 is a data flow diagram illustrating an example system architecture in accordance with embodiments of the present disclosure. The system includes a function generator 402, an amplifier 404, a transmitter matching unit 406, and a transmitter transducer 408 acoustically coupled to a rock sample 410. On the receiver side, a receiver transducer 412 is acoustically coupled to the sample 410, and is connected to electronics including a receiver matching unit 418, a filter 416, and oscilloscope 414.

A sinusoidal tone-burst signal, generated by the function generator 402, passes through a power amplifier 404. The amplified high-voltage signal passed through a transmitter matching unit to suppress the transient behavior caused by the mismatch in electrical impedances between the amplifier and the transducer. The amplified signal then drives a piezo-electric acoustic transducer 408 with a central frequency of 1 MHz.

To ensure wave propagation in a single direction, the number of cycles of the excitation signal was selected to fit the height of the specimen such that the spatial length of the tone burst was less than the specimen height. This approach eliminates possible spurious (apparent) harmonic signals at higher harmonics caused by the interference between the excitation and reflected waves, as well as the effects of boundary conditions. The rock sample dimension prevents selection of the lower frequency (larger wavelength) in the measurement.

A second transducer 412, with its central frequency at 2.25 MHz, was used as the receiver. This broadband transducer received the fundamental and the second harmonic signal. The receiver was terminated with a matching unit 418 as well, to suppress the instrumentation non-linearity, and electrically coupled through the matching unit and a filter 416, to an oscilloscope 414. A special fixture was designed to hold the rock specimen vertically. The transducer was pressed down by constant pressure on the top of the specimen during bonding and testing. The filtered voltage and current signals of the transmitted ultrasonic waves were recorded and averaged 256 times with an oscilloscope 414, and underwent further signal processing.

Core samples used in tests of the techniques in accordance with embodiments of the present disclosure include Indiana limestone, Mancos shale, Alabama marble, Crab Orchard sandstone, and Mansfield sandstone. In addition, three Barnett shale samples with pre-measured nuclear magnetic resonance (NMR) porosity were prepared for measurement.

One aspect of measuring second harmonic generation is to sufficiently calibrate instrumentation non-linearity to ensure that the material non-linearity dominates the measurement. To achieve this, the Bermes technique for second harmonic system non-linearity calibration may be employed by varying the applied voltage. This may include determining an optimal input voltage for receiver electronics producing the detected acoustic signal at a receiver to optimize non-linear harmonic interference to the second harmonic mode. This may be carried out by estimating initial acoustic wave non-linearity parameters ($\beta_n$) for the volume at each of a plurality input voltages until a stability condition is met for the initial acoustic wave non-linearity parameters, and using at least one of the plurality of voltages corresponding to the stability condition being met for producing the detected acoustic signal. The stability condition may be met when a variation measure (e.g., standard deviation) between parameters corresponding to successive voltages is less than a threshold value. As another example, the stability condition may be met when an increase in voltage by an incremental amount produces a change in initial acoustic wave non-linearity parameter value in comparison with the previous initial acoustic wave non-linearity parameter value less than a threshold percentage (such as, for example, 3, 5, 10, 15, or 20 percent). Modal amplitude ratio $A_2/A_1^2$ (an estimate of parameter β) may be used as a relative measure of material non-linearity. Plotting the modal amplitude ratio $A_2/A_1^2$ as a function of the fundamental wave amplitude $A_1$ results in a logarithmic decay, indicating the non-linearity of the measurement system.

In example test data, the modal amplitude ratio $A_2/A_1^2$ may exhibit two regions with varying the primary excitation amplitude. The ratio remains flat in region 1 and increases rapidly as the output level is reduced in region 2. In region 1, the instrumentation non-linearity is sufficiently small such that enlarging output levels has no significant influence on the modal amplitude ratio (e.g., measured change is below a threshold level). Acoustic non-linearity measurements were conducted on all rock samples.

Figure 5A:
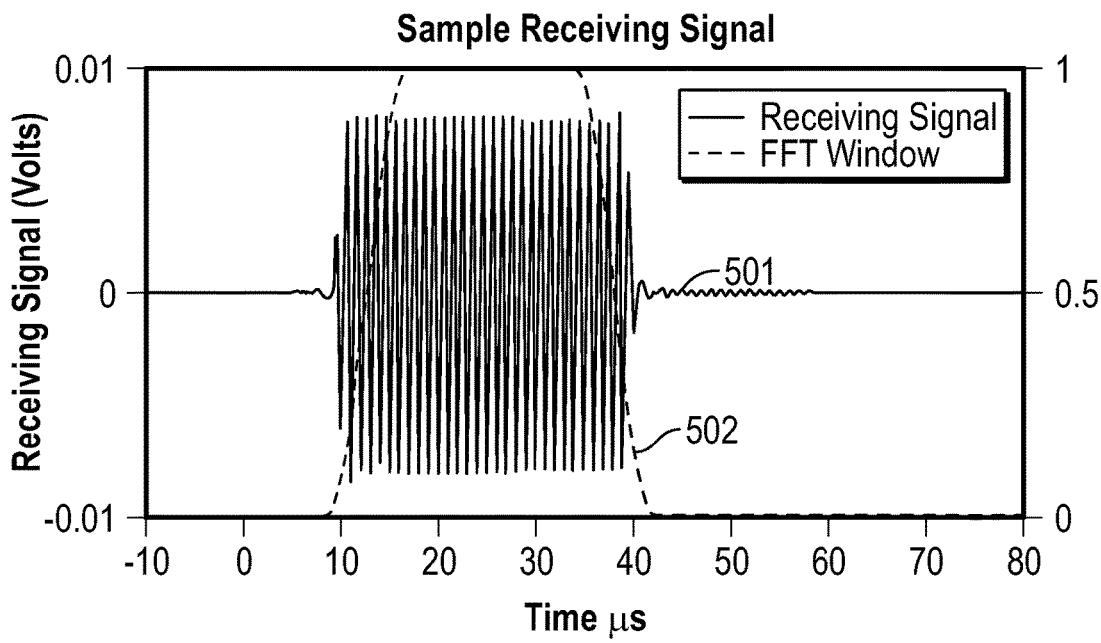
FIGS. 5A & 5B illustrate signals acquired from a Mancos shale sample using techniques in accordance with embodiments of the present disclosure.
Figure 5B:
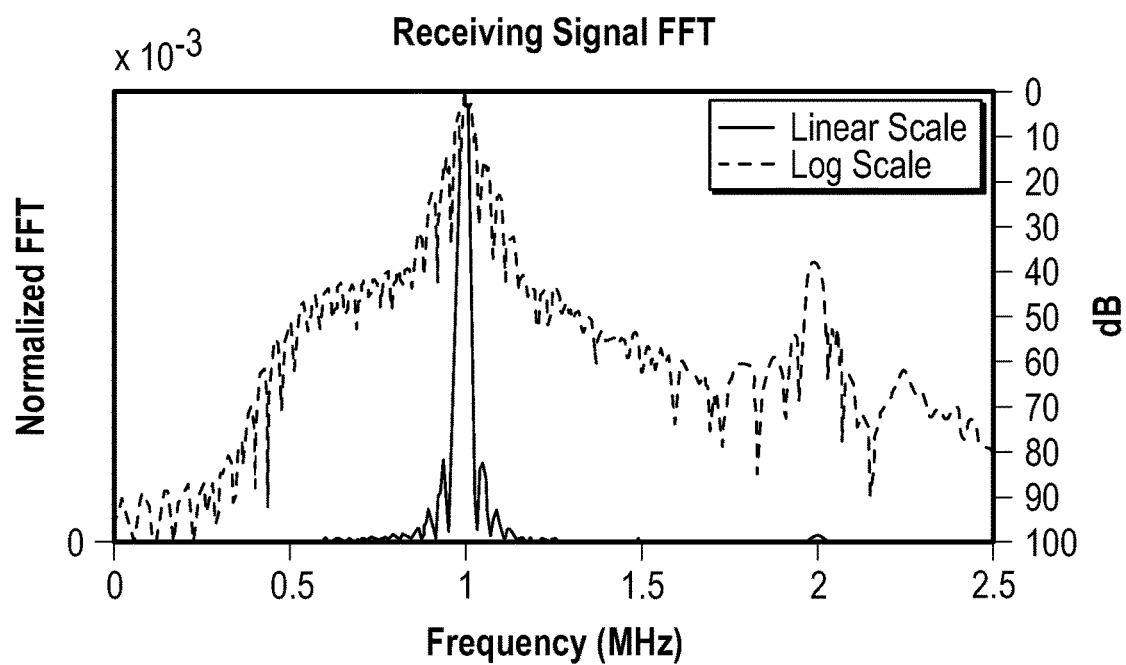

FIGS. 5A & 5B illustrate signals acquired from a Mancos shale sample using techniques in accordance with embodiments of the present disclosure. FIG. 5A illustrates a sample scan (time domain) signal 701. To maintain a consistent signal processing procedure, a uniform Tukey window 702 of a constant length was used for all the signal processing procedures to extract the first arriving wave packet for the Fourier transform. FIG. 5B illustrates a corresponding frequency spectrum. Evident second harmonics are generated, which result from the highly inherent non-linearity of the rock samples. Tests were conducted on all rock samples.

Figure 6:
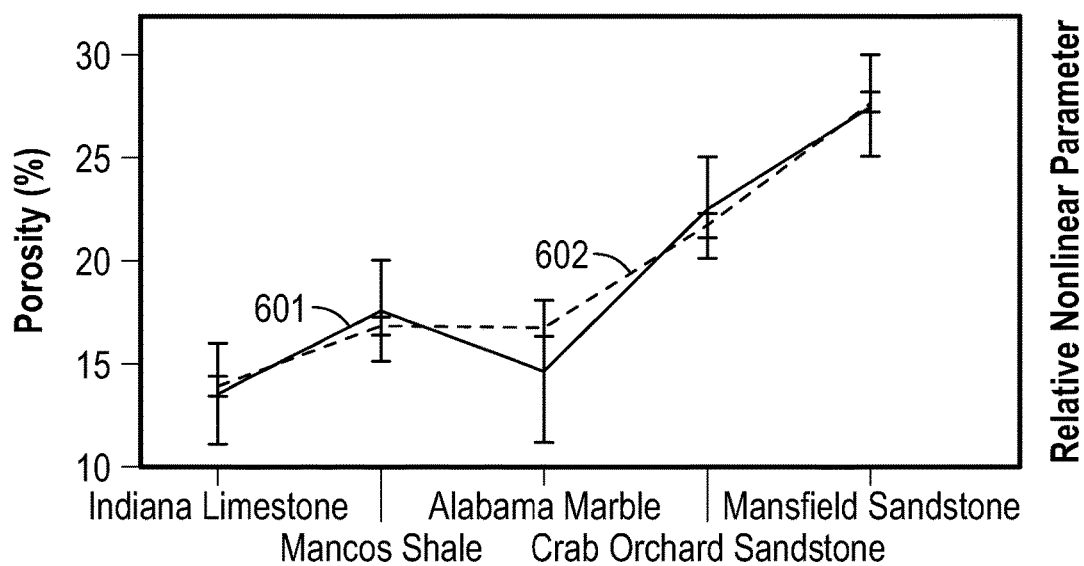
FIG. 6 compares estimated porosity in accordance with embodiments of the present disclosure with respect to conventional reference values.

FIG. 6 compares estimated porosity 602 in accordance with embodiments of the present disclosure with respect to conventional reference values 601. Estimated porosity for the rock samples compares favorably porosity values from literature review. The Indiana limestone samples exhibited the lowest second harmonic generation as indicated in FIG. 6. On the other hand, the Mansfield sandstone samples have the highest second harmonics, which corresponds to their highest porosity and non-linear elastic properties. The error bar shows the range of the measurement results.

The expected correlation between acoustic non-linear generation and the porosity/non-linearity of the rock samples was confirmed with following experiments. The acoustic non-linearity measurements were performed with increasing transducer input voltage and demonstrated low influence of instrumentation on non-linearity. It should be noted that the estimated non-linearity parameter β (e.g., estimated as $A_2/A_1^2$) remains nearly constant when varying the input voltage. This condition indicates that the instrumentation non-linearity is sufficiently small such that its amplification by higher input voltage does not have significant influence on the relative non-linearity parameters. This response again confirms that the acoustic non-linearity of the rock samples can be effectively measured. It should also be noted that the non-linear generations are sensitive to porosity and the third-order elastic constants of the rock formations. When comparing the estimated non-linearity parameter results to the porosity of the rock formation, the relative non-linearity parameter increases with porosity. This growth agrees with the theoretical and numerical predictions that formation porosity results in local stress concentrations that lead to greater material non-linearity.

Figure 7A:
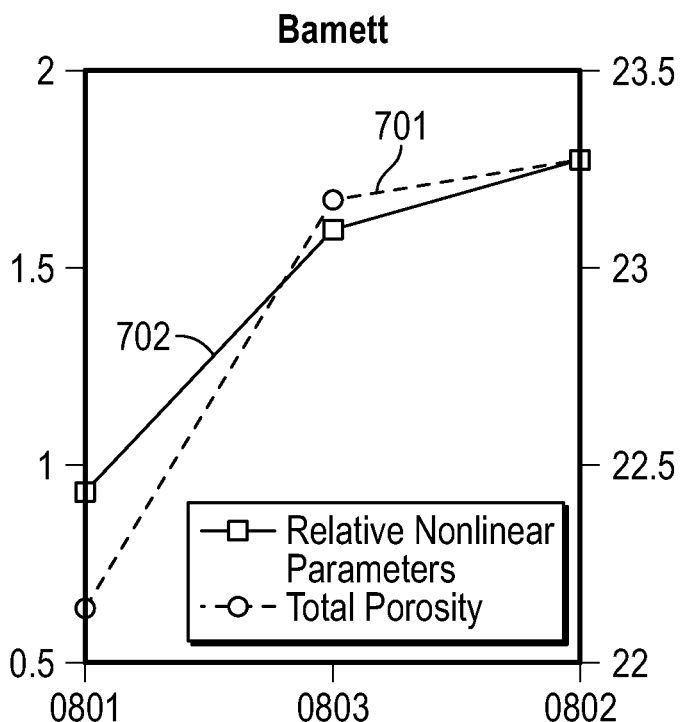
FIG. 7A compares estimated porosity of Barnett core samples using non-linear acoustic techniques in accordance with embodiments of the present disclosure with NMR porosity measurement results.
Figure 7B:
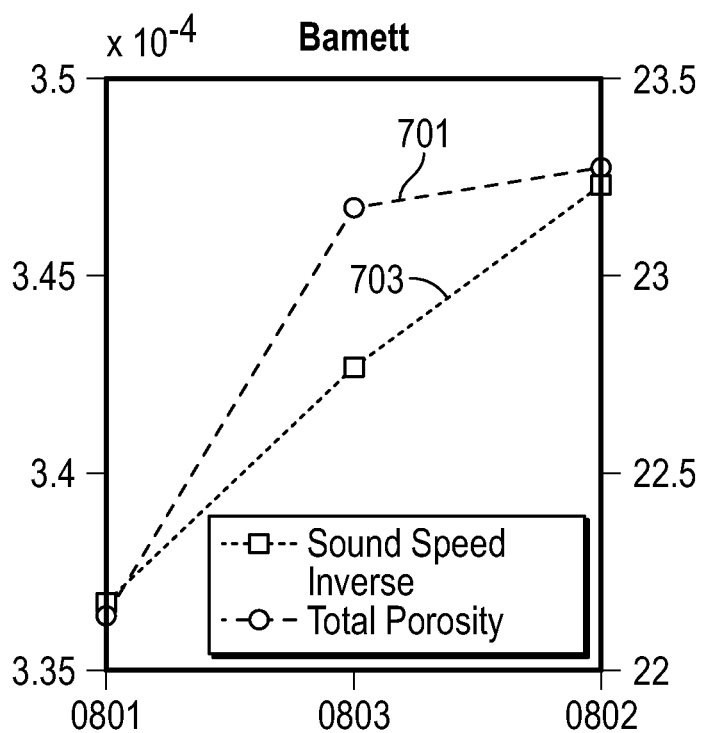
FIG. 7B compares estimated porosity of Barnett core samples using sound speed measurements with NMR porosity measurement results.

FIG. 7A compares estimated porosity of Barnett core samples using non-linear acoustic techniques in accordance with embodiments of the present disclosure with NMR porosity measurement results. FIG. 7B compares estimated porosity of Barnett core samples using sound speed measurements with NMR porosity measurement results.

Three Barnett samples (Barnett-0801, Barnett-0802, and Barnett-0803) with very close NMR measured porosity were measured using the non-linear methods of the present disclosure and conventional sound speed methods. Both estimated non-linearity parameter results and sound speed results are shown in FIGS. 7A & 7B, which are both compared with NMR porosity results. P-wave sound speed results are calculated from the time delay between the transmitting signal and receiving signal. The inverse of P-wave sound speed is used here to correlate with NMR-measured porosity. The results employing estimated parameter β in accordance with the techniques of the present disclosure have better agreement with NMR porosity. The results show that non-linear measurements are very sensitive to even minor porosity differences in the same type of formation samples.

As described above, core samples may be analyzed at the surface or downhole while the sample is within a coring tool. The acoustic testing system above may be incorporated around a chamber holding an acquired core sample as part of a system in accordance with FIGS. 1A & 1B.

Herein, the term "information" may include one or more of: raw data, processed data, and signals. The term "information" as used herein includes any form of information (analog, digital, EM, printed, etc.). As used herein, a processor is any information processing device that transmits, receives, manipulates, converts, calculates, modulates, transposes, carries, stores, or otherwise utilizes information. In several non-limiting aspects of the disclosure, a processor includes a computer that executes programmed instructions for performing various methods. These instructions may provide for equipment operation, control, data collection and analysis and other functions in addition to the functions described in this disclosure. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on.

Thus, configuration of the processor may include operative connection with resident memory and peripherals for executing programmed instructions. In some embodiments, estimation of the parameter of interest may involve applying a model. The model may include, but is not limited to, (i) a mathematical equation, (ii) an algorithm, (iii) a database of associated parameters, (iv) an array, or a combination thereof which describes physical characteristics the formation, the borehole, borehole fluid, casing or other borehole equipment or infrastructure (standing alone or as installed) in relation to an estimated non-linearity parameter (β) from information obtained by the sensors as described herein.

Parameters of interest, including values for the estimated non-linearity parameter (β), may be stored (recorded) as information or visually depicted on a display. Aspects of the present disclosure relate to modeling a volume of an earth formation using an estimated parameter of interest, such as, for example, by associating estimated parameter values with portions of the volume of interest to which they correspond. The model of the earth formation generated and maintained in aspects of the disclosure may be implemented as a representation of the earth formation stored as information. Any of the information (e.g., data, signals, parameters, etc.) may be stored on a non-transitory machine-readable medium, and/or rendered (e.g., visually depicted) on a display.

Control of components of apparatus and systems described herein may be carried out using one or more models as described above. For example, at least one processor may be configured to modify operations i) autonomously upon triggering conditions, ii) in response to operator commands, or iii) combinations of these. Such modifications may include changing drilling parameters, steering the drillbit (e.g., geosteering), changing a mud program, optimizing measurements, and so on. Control of these devices, and of the various processes of the drilling system generally, may be carried out in a completely automated fashion or through interaction with personnel via notifications, graphical representations, user interfaces and the like. Reference information accessible to the processor may also be used.

The processing of the measurements made in wireline or MWD applications may be done by a surface processor, by a downhole processor, or at a remote location. The data acquisition may be controlled at least in part by the downhole electronics. Implicit in the control and processing of the data is the use of a computer program on a suitable non-transitory machine readable medium that enables the processors to perform the control and processing. The non-transitory machine readable medium may include ROMs, EPROMs, EEPROMs, flash memories and optical disks. The term processor is intended to include devices such as a field programmable gate array ('FPGA').

The term "conveyance device" or "carrier" as used above means any device, device component, combination of devices, media and/or member that may be used to convey, house, support or otherwise facilitate the use of another device, device component, combination of devices, media and/or member. Exemplary non-limiting carriers include drill strings of the coiled tube type, of the jointed pipe type and any combination or portion thereof. Other conveyance device examples include casing pipes, wirelines, wire line sondes, slickline sondes, drop shots, downhole subs, BHA's, drill string inserts, modules, internal housings and substrate portions thereof, and self-propelled tractors.

The term "near real-time" as applied to downhole evaluation described herein refers to generation of the adjusted image while the BHA is still downhole and prior to the drill bit extending the borehole a distance of 1 meter, 0.5 meters, 0.25 meters, 0.1 meters, or less.

The term "azimuthal distribution" refers to distribution over three or more points about a center, wherein any two consecutive points are less than 180 degrees apart. The term "substantially longitudinal axis" as applied to the rotational axis of a rotating transducers means an axis sufficiently close to a longitudinal axis of the carrier to receive at each of the plurality of azimuthally distributed orientations a reflection of a corresponding emitted wave from portions of a borehole wall adjacent the carrier.

As used herein, the term "fluid" and "fluids" refers to one or more gasses, one or more liquids, and mixtures thereof. A "downhole fluid" as used herein includes any gas, liquid, flowable solid and other materials having a fluid property, and relating to hydrocarbon recovery. A downhole fluid may be natural or man-made and may be transported downhole or may be recovered from a downhole location. Non-limiting examples of downhole fluids include drilling fluids, return fluids, formation fluids, production fluids containing one or more hydrocarbons, oils and solvents used in conjunction with downhole tools, water, brine, and combinations thereof.

In a typical operation, core samples may be obtained by extracting a core (which may be cylindrical in shape) of a particular or customary diameter and cutting a conventional length from that core. This may be known as a bulk sample. A plug sample may be taken from the bulk sample and subjected to mechanical testing. Use of the term "core sample" herein refers to any of these objects (core, bulk sample, plug sample, and so on), although plug samples may be convenient for use with typical instruments currently available.

Measurements of sonic travel time, or "slowness," are well known, and may be considered as depending upon the properties inherent in Snell's Law to propagate sound from a transmitter to a receiver through an earth formation. Slowness is the inverse of the sound velocity. The measurement is representative of travel time of sound through the formation. Typically the term refers to measurements wherein the transmitter and receiver are in a borehole intersecting the formation, e.g., on a tool string in the borehole. The speed of sound in the earth formation is governed in approximation by the physical properties embodied in the Wood-Biot-Gassmann equations.

In some embodiments, the borehole may be utilized to recover hydrocarbons. In other embodiments, the borehole may be used for geothermal applications, water production, mining, tunnel construction, or other uses.

The present disclosure is susceptible to embodiments of different forms. There are shown in the drawings, and herein are described in detail, specific embodiments of the present disclosure with the understanding that the present disclosure is to be considered an exemplification of the principles of the disclosure and is not intended to limit the disclosure to that illustrated and described herein. While the foregoing disclosure is directed to the one mode embodiments of the disclosure, various modifications will be apparent to those skilled in the art. It is intended that all variations be embraced by the foregoing disclosure.

We claim:

1. A method of evaluating a volume of interest of an earth formation comprising:
    activating a transmitter to propagate an acoustic wave through the volume;
    producing a detected acoustic signal at a receiver responsive to the acoustic wave;
    estimating a parameter of interest of the volume using a value of a signal property for a second harmonic mode signal component of the detected acoustic signal by:
        estimating an acoustic wave non-linearity parameter ($\beta$) for the volume using a relationship between the value of the signal property of the second harmonic mode signal component and a value of the signal property for a fundamental mode signal component of the detected acoustic signal, wherein the relationship comprises a ratio of the value of the signal property of the second harmonic mode signal component and a square of the value of the signal property for a fundamental mode signal component; and
        estimating the parameter of interest using a correlation between the acoustic wave non-linearity parameter ($\beta$) and the parameter of interest.

2. The method of claim 1 comprising identifying the fundamental mode signal and the second harmonic mode signal associated with the detected acoustic signal.

3. The method of claim 1 wherein the signal property comprises frequency amplitude.

4. The method of claim 1 wherein the parameter of interest comprises at least one of: i) porosity; ii) tortuosity; iii) water saturation; iv) oil saturation; v) a formation stress; vi) a fluid parameter.

5. The method of claim 1 comprising positioning at least one of the transmitter proximate to a wall of the borehole for transmission.

6. The method of claim 1 wherein the volume is remote from the formation while activating the transmitter and producing the signal.

7. The method of claim 1 wherein the detected acoustic signal is detected during a downhole operation in the formation, the downhole operation comprising at least one of: i) performing a drilling operation, ii) wireline logging, iii) cement evaluation; and iv) downhole core analysis.

8. The method of claim 1 comprising determining an optimal input voltage for receiver electronics producing the detected acoustic signal at a receiver to optimize non-linear harmonic interference to the second harmonic mode by:
   estimating initial acoustic wave non-linearity parameters ($\beta_n$) for the volume at each of a plurality input voltages until a stability condition is met for the initial acoustic wave non-linearity parameters ($\beta_n$); and
   using at least one of the plurality of voltages corresponding to the stability condition being met for producing the detected acoustic signal.

9. The method of claim 8 wherein the stability condition comprises:
   a variation measure between initial acoustic wave non-linearity parameters ($\beta_n$) corresponding to successive voltages is less than a threshold value.

10. The method of claim 1 comprising:
   activating a transmitter to propagate an acoustic wave through the volume at each of a plurality of frequencies;
   generating acoustic signals at a receiver responsive to the acoustic wave corresponding to each of the plurality of frequencies;
   identifying one of the acoustic signals as meeting selection criteria for a detected acoustic signal; and
   producing the identified one of the acoustic signals as the detected acoustic signal.

11. The method of claim 1 further comprising estimating the parameter of interest of the volume in dependence upon the value of the signal property for the second harmonic mode signal component and a value of at least one of: i) a shear wave slowness for the volume; and ii) a compressional wave slowness for the volume.

12. An apparatus for evaluating a volume of interest of an earth formation, the apparatus comprising:
   a transmitter configured to propagate an acoustic wave through the volume;
   a receiver configured to detect acoustic signals from the volume responsive to the propagated acoustic wave;
   at least one processor configured to estimate a parameter of interest of the volume using a value of a signal property for a second harmonic mode signal component of a detected acoustic signal by:
      estimating an acoustic wave non-linearity parameter ($\beta$) for the volume using a relationship between the value of the signal property of the second harmonic mode signal component and a value of the signal property for a fundamental mode signal component of the detected acoustic signal, wherein the relationship comprises a ratio of the value of the signal property of the second harmonic mode signal component and a square of the value of the signal property for a fundamental mode signal component; and
      estimating the parameter of interest using a correlation between the acoustic wave non-linearity parameter ($\beta$) and the parameter of interest.

13. A method of evaluating a volume of interest of an earth formation comprising:
   activating a transmitter to propagate an acoustic wave through the volume;
   producing a detected acoustic signal at a receiver responsive to the acoustic wave;
   estimating a parameter of interest of the volume using a value of a signal property for a second harmonic mode signal component of the detected acoustic signal by:
      estimating an acoustic wave non-linearity parameter ($\beta$) for the volume using a relationship between the value of the signal property of the second harmonic mode signal component and a value of the signal property for a fundamental mode signal component of the detected acoustic signal; and
      estimating the parameter of interest using a correlation between the acoustic wave non-linearity parameter ($\beta$) and the parameter of interest;
   wherein the method further comprises determining an optimal input voltage for receiver electronics producing the detected acoustic signal at a receiver to optimize non-linear harmonic interference to the second harmonic mode by:
      estimating initial acoustic wave non-linearity parameters for the volume at each of a plurality input voltages until a stability condition is met for the initial acoustic wave non-linearity parameters; and
      using at least one of the plurality of voltages corresponding to the stability condition being met for producing the detected acoustic signal.

* * * * *

UNITED STATES PATENT AND TRADEMARK OFFICE
CERTIFICATE OF CORRECTION

PATENT NO. : 10,317,556 B2
APPLICATION NO. : 15/010730
DATED : June 11, 2019
INVENTOR(S) : Xiaochu Yao et al.

It is certified that error appears in the above-identified patent and that said Letters Patent is hereby corrected as shown below:

In the Claims

At Column 20, Line 54, please delete "a" and insert --the--

At Column 20, Line 60, after "signal" insert --component--

At Column 20, Line 61, after "signal" insert --component--

At Column 21, Line 1, please delete "at least one of"

At Column 21, Line 2, please delete "the" and insert --a--

At Column 21, Line 6, after "producing the" insert --detected acoustic--

At Column 21, Line 14, please delete "a" and insert --the--

At Column 21, Line 15, after "mode" insert --signal component--

At Column 21, Line 17, after "plurality" insert --of--

At Column 21, Line 20, after "plurality of" insert --input--

At Column 21, Line 29, please delete "a" and insert --the--

At Column 21, Line 29, please delete "an" and insert --the--

At Column 21, Line 30, after "volume" insert --of interest--

At Column 21, Line 32, please delete "a" and insert --the--

Signed and Sealed this
Fifth Day of November, 2019

Andrei Iancu
*Director of the United States Patent and Trademark Office*

CERTIFICATE OF CORRECTION (continued)
U.S. Pat. No. 10,317,556 B2

At Column 21, Line 36, please delete "a" and insert --the--

At Column 22, Line 14, please delete "a" and insert --the--

At Column 22, Line 39, please delete "a" and insert --the--

At Column 22, Line 41, after "mode" insert --signal component--

At Column 22, Line 43, after "plurality" insert --of--

At Column 22, Line 43, after "plurality of" insert --input--